United States Patent
Ebisawa

(10) Patent No.: US 9,885,780 B2
(45) Date of Patent: Feb. 6, 2018

(54) OBJECT INFORMATION ACQUIRING APPARATUS

(71) Applicant: CANON KABUSHIKI KAISHA, Tokyo (JP)

(72) Inventor: Hisafumi Ebisawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/222,398

(22) Filed: Mar. 21, 2014

(65) Prior Publication Data

US 2014/0288426 A1     Sep. 25, 2014

(30) Foreign Application Priority Data

Mar. 25, 2013   (JP) .................................. 2013-062580

(51) Int. Cl.
*A61B 8/00* (2006.01)
*G01S 7/52* (2006.01)
(Continued)

(52) U.S. Cl.
CPC ...... *G01S 7/52038* (2013.01); *G01S 7/52026* (2013.01); *G01S 7/52031* (2013.01); *G01S 7/52036* (2013.01); *G01S 7/52046* (2013.01); *G01S 7/52047* (2013.01); *G01S 15/895* (2013.01); *G01S 15/8915* (2013.01); *G01S 15/8938* (2013.01); *G01S 15/8963* (2013.01); *G01S 15/8979* (2013.01);
(Continued)

(58) Field of Classification Search
USPC ........................................................ 600/438
See application file for complete search history.

(56) References Cited

U.S. PATENT DOCUMENTS 4,399,822 A * 8/1983 Theumer .................. A61B 8/00
                                                    600/445
6,277,073 B1 * 8/2001 Bolorforosh ........ G01S 7/52047
                                                    600/437
(Continued)

FOREIGN PATENT DOCUMENTS

JP    S55-116613 U    8/1980
JP    S61-217144 A    9/1986
(Continued)

*Primary Examiner* — Joel F Brutus
(74) *Attorney, Agent, or Firm* — Canon USA, Inc. I.P. Division

(57) ABSTRACT

An object information acquiring apparatus includes a probe configured to irradiate ultrasonic waves to an object, receive ultrasonic echoes, and convert the ultrasonic echoes into electric signals, a scanning unit configured to cause the probe to perform back-and-forth scanning on the object, an ultrasonic control unit configured to control irradiation of ultrasonic waves, a signal processing unit configured to obtain an ultrasonic, and a combining unit configured to combine a plurality of ultrasonic images. The scanning unit causes the probe to perform back-and-forth scanning on the object such that regions subjected to ultrasonic irradiation performed by the probe in forward and backward paths in the back-and-forth scanning overlap with each other. The ultrasonic control unit employs different methods for irradiating ultrasonic waves in the forward and backward paths. The combining unit combines a plurality of ultrasonic images with one another.

34 Claims, 10 Drawing Sheets

(51) Int. Cl.
   *G01S 15/89*    (2006.01)
   *A61B 8/08*     (2006.01)
(52) U.S. Cl.
   CPC ...... *G01S 15/8993* (2013.01); *G01S 15/8995* (2013.01); *A61B 8/485* (2013.01)

(56) References Cited

U.S. PATENT DOCUMENTS

| | | | |
|---|---|---|---|
| 2004/0215075 A1* | 10/2004 | Zagzebski | A61B 5/0048 600/442 |
| 2009/0043209 A1* | 2/2009 | Hirama | A61B 8/483 600/459 |
| 2011/0079083 A1* | 4/2011 | Yoo | G01S 7/52065 73/632 |
| 2011/0208057 A1* | 8/2011 | Oikawa | A61B 5/0095 600/443 |

FOREIGN PATENT DOCUMENTS

| | | |
|---|---|---|
| JP | 2002-153473 A | 5/2002 |
| JP | 2003-19132 A | 1/2003 |
| JP | 2005-87636 A | 4/2005 |
| JP | 2006-6932 A | 1/2006 |
| JP | 2006-247061 A | 9/2006 |
| JP | 2006-346161 A | 12/2006 |
| JP | 2011-045659 A | 3/2011 |
| JP | 2012-196246 A | 10/2012 |

\* cited by examiner

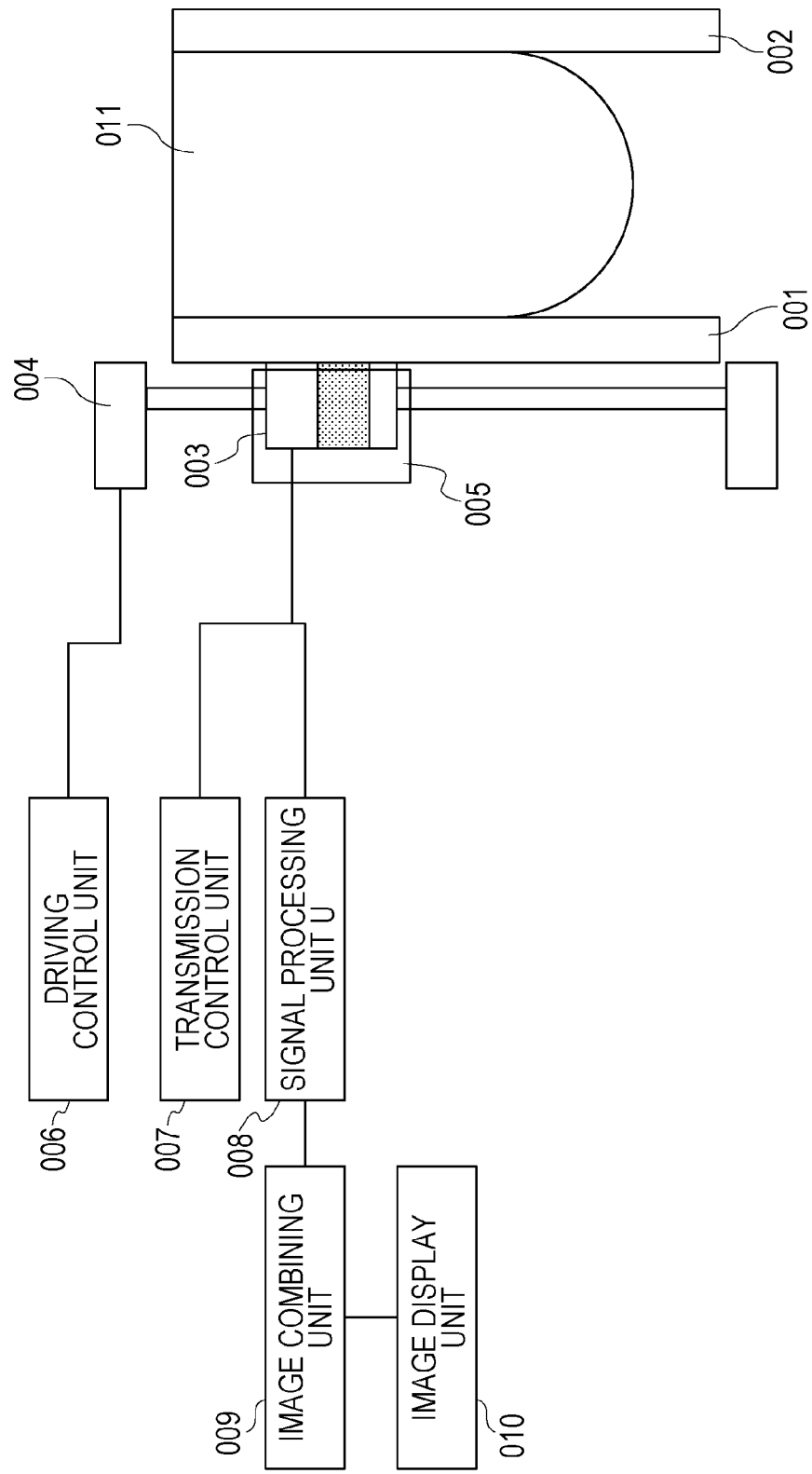

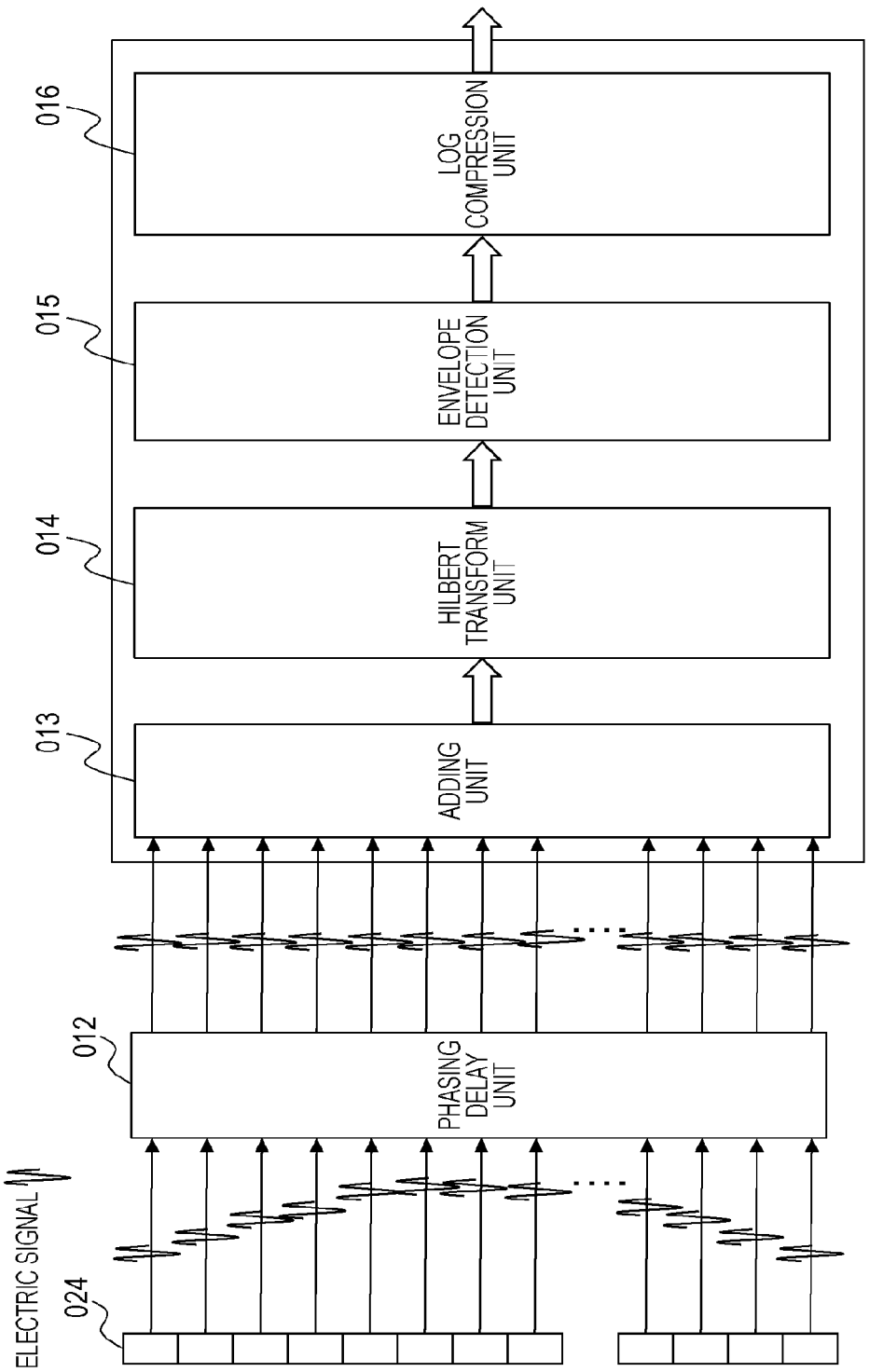

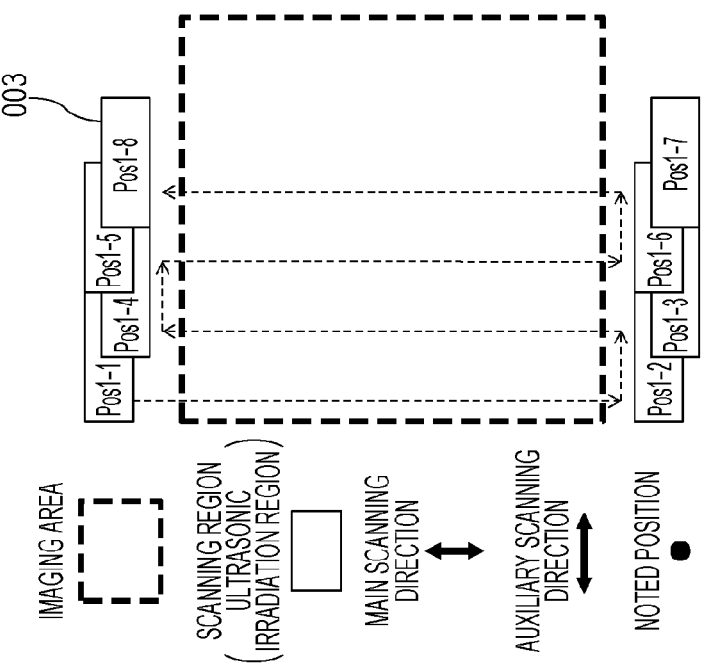
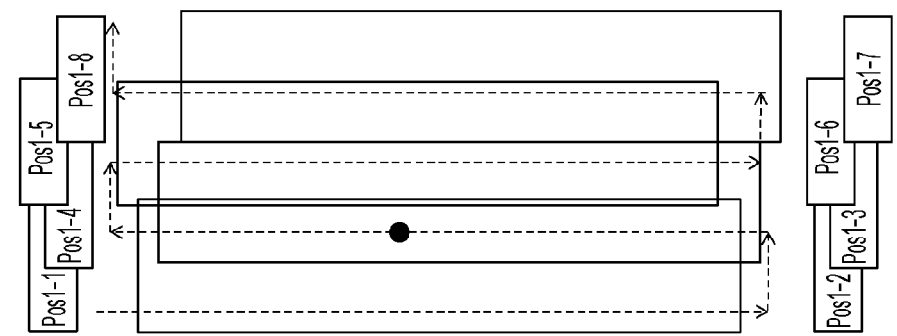
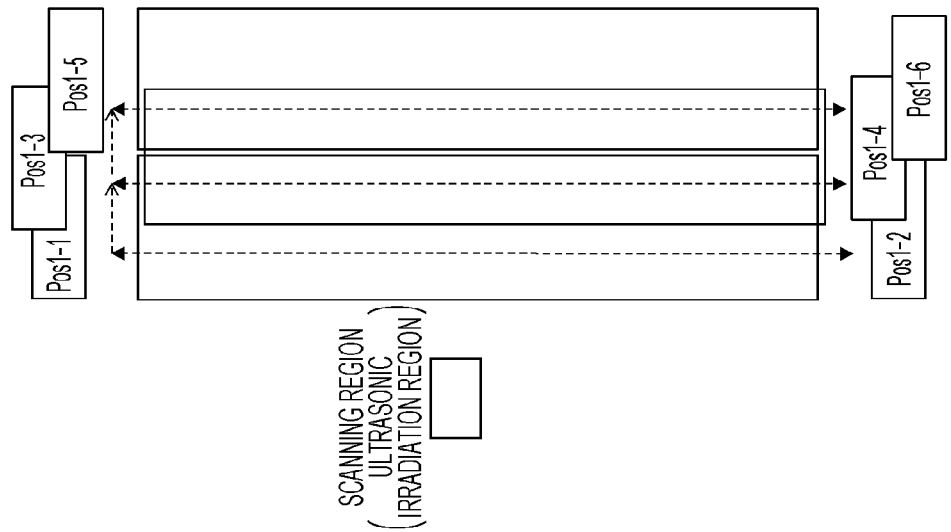

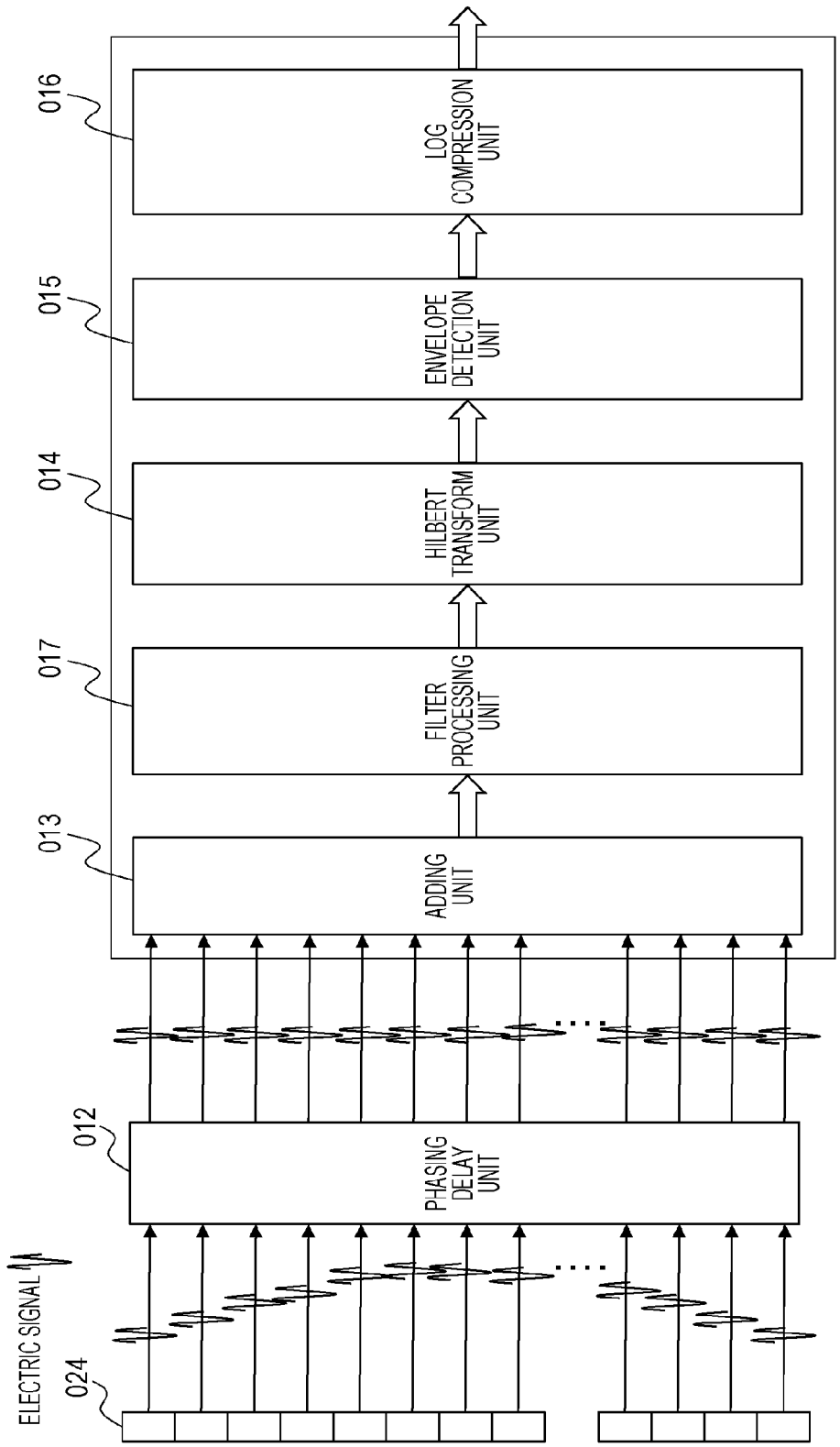

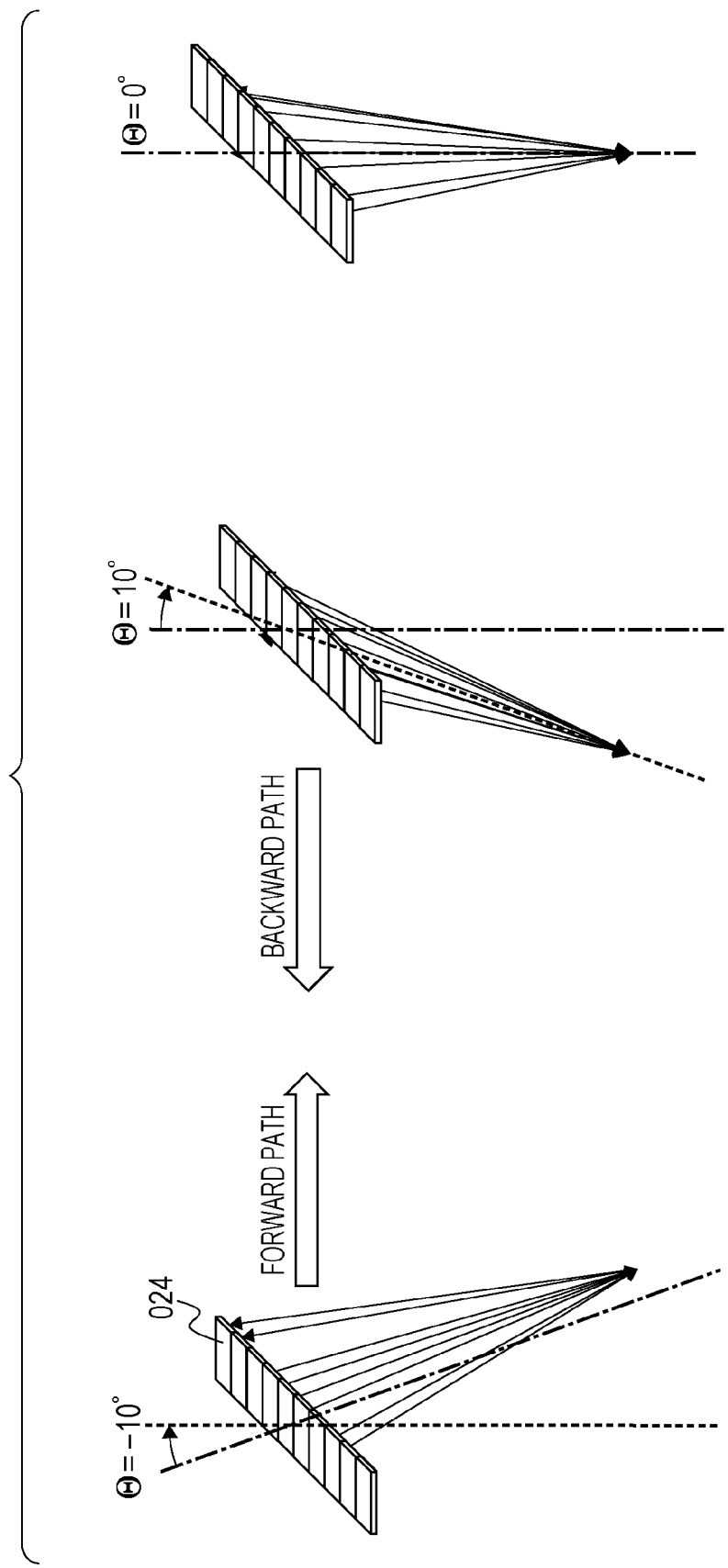

OBJECT INFORMATION ACQUIRING APPARATUS

BACKGROUND

Field of Art

The present disclosure relates to an object information acquiring apparatus.

Description of the Related Art

In general, ultrasonic diagnostic apparatuses have been widely used. The diagnostic apparatuses do not irradiate x rays, and therefore, have attracted attention as diagnostic apparatuses which are at low risk of being exposed to radiation. As an example of such a diagnostic apparatus, Japanese Patent Laid-Open No. 2011-45659 discloses a scanning-type ultrasonic object information acquiring apparatus which causes a probe to scan an object so that three-dimensional image data items are obtained in a wide range and mixing (compounding) overlapping data items so that a high-quality image is realized.

In the technique disclosed in Japanese Patent Laid-Open No. 2011-45659, an object is scanned by a one-dimensional array probe or a two-dimensional array probe so that a three-dimensional image data group is obtained in a wide range. Then data items in an overlapping region (overlapping portion) of the three-dimensional image data group are combined with one another, that is, information items in the same portion (coordinate) are obtained from different positions of a probe and combined with one another so that a high-quality image is realized.

However, further improvement is demanded for realizing an image of higher quality.

SUMMARY

The present disclosure provides an object information acquiring apparatus including a probe configured to irradiate ultrasonic waves to an object, receive ultrasonic echoes obtained when the object reflects the ultrasonic waves, and convert the ultrasonic echoes into electric signals, a scanning unit configured to cause the probe to perform back-and-forth scanning on the object, an ultrasonic control unit configured to control irradiation of ultrasonic waves to the object performed by the probe, a signal processing unit configured to obtain an ultrasonic image based on the electric signals, and a combining unit configured to combine a plurality of ultrasonic images obtained by the signal processing unit. The scanning unit causes the probe to perform back-and-forth scanning on the object such that regions subjected to ultrasonic irradiation performed by the probe in forward and backward paths in the back-and-forth scanning overlap with each other. The ultrasonic control unit employs different methods for irradiating ultrasonic waves to the object from the probe in the forward and backward paths. The combining unit combines a plurality of ultrasonic images obtained in accordance with electric signals based on ultrasonic waves irradiated in the different irradiation methods.

Further features of the present invention will become apparent from the following description of exemplary embodiments with reference to the attached drawings.

BRIEF DESCRIPTION OF THE DRAWINGS

FIG. 1 is a diagram illustrating a configuration of an object information acquiring apparatus according to an embodiment of the present invention.

FIG. 2 is a diagram illustrating a configuration of a signal processing unit according to an embodiment of the present invention.

FIGS. 3A to 3C are diagrams illustrating scanning methods of a probe according to an embodiment of the present invention.

FIG. 4 is a diagram illustrating another configuration of the signal processing unit according to an embodiment of the present invention.

FIG. 10 is a diagram illustrating a state in which ultrasonic waves irradiated from a probe are inclined in a scanning direction according to an embodiment of the present invention.

DESCRIPTION OF THE EMBODIMENTS

Figure 5A:
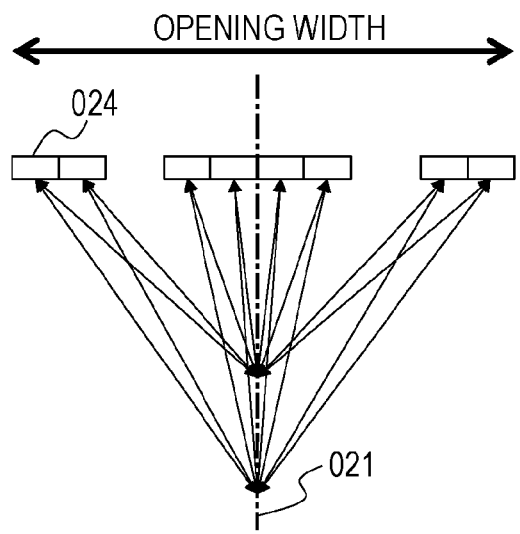
FIGS. 5A to 5C are diagrams illustrating positions of a scanning line of an image to be obtained.

As an example of an object information acquiring apparatus according to an embodiment of the present invention, an ultrasonic image apparatus system which is configured such that an object is held by two holding members and scanning is performed in a direction along the holding members using a probe so as to obtain object information will be described with reference to FIG. 1.

Configuration of Apparatus

Holding members 001 and 002 hold an object 011, and an ultrasonic probe 003 irradiates ultrasonic waves to the object 011, receives ultrasonic echoes (echo) which are transmitted when the object 011 reflects the ultrasonic waves, and converts the ultrasonic echoes into electric signals. The ultrasonic probe 003 includes a large number of piezoelectric elements 024 and converts echo signals received by the piezoelectric elements 024 into electric signals. The ultrasonic probe 003 is fixed on a carriage 005. A driving mechanism 004 moves the carriage 005. A driving control unit 006 controls the driving mechanism 004, and the driving mechanism 004 and the driving control unit 006 move the carriage 005 along the holding member 001 to an arbitrary position in an imaging area. Specifically, the driving mechanism 004 and the driving control unit 006 constitute a scanning section which causes the probe 003 to scan the object 011. A transmission control unit 007 serving as an ultrasonic control section controls irradiation of ultrasonic waves to the object 011 from the probe 003. A signal processing unit U 008 serving as a signal processing section obtains an ultrasonic image based on electric signals output from the probe 003. An image combining unit 009 serving as a combining section combines a plurality of ultrasonic images obtained by the signal processing section. An image display unit 010 displays combined image data. The driving control unit 006 included in the scanning section causes the probe 003 to perform scanning forward and backward on the object 011 so that regions to which ultrasonic waves are irradiated by the probe 003 in the forward scanning and the backward scanning overlap with each other. Furthermore, the transmission control unit 007 serving as the ultrasonic control section employs different methods for irradiating ultrasonic waves on the object 011 by the probe 003 in the forward path and the backward path. Furthermore, the image combining unit 009 serving as the combining section combines a plurality of ultrasonic images obtained in accordance with the electric signals based on the ultrasonic waves irradiated by the different irradiation methods. By this, a high-quality ultrasonic image may be obtained while a speed of scanning performed by the probe 003 is not reduced and complicated signal processing is not performed. Specifically, since the ultrasonic irradiation regions in the forward and backward paths overlap with each other and the different ultrasonic-wave irradiation conditions (transmission conditions) are employed in the forward and backward paths, optimum images may be selected from among a plurality of images in the same region and may be combined with one another. Accordingly, a high-quality ultrasonic image may be obtained while a speed of scanning performed by the probe 003 is not reduced and complicated signal processing is not performed.

FIG. 2 is a diagram illustrating a configuration of the signal processing unit U 008. The piezoelectric elements 024 constitute the probe 003. A phasing delay unit 012 makes uniform phases of electric signals received by the piezoelectric elements 024. An adding unit 013 adds delayed signals to one another. A Hilbert transform unit 014 performs Hilbert transform on a signal obtained by the addition, and an envelope detection unit 015 performs envelope detection. A LOG compression unit 016 performs LOG compression on a signal which has been subjected to the envelope detection.

Reconstruction of Image

First, a procedure of reconstructing (obtaining) an image from echo signals which are obtained as a result of ultrasonic irradiation and which are transmitted from the object 011 will be described with reference to FIG. 1.

The transmission control unit 007 determines delay times for driving a group of the piezoelectric elements 024 constituting a transmission opening to converge transmission beams on a focus position. The transmission control unit 007 transmits electric signals to the piezoelectric elements 024 in accordance with the delay times. The piezoelectric elements 024 convert the electric signals into ultrasonic signals and irradiate the ultrasonic signals to the object 011 through the holding member 001.

Since the holding member 001 allows ultrasonic waves to pass, the holding member 001 is preferably formed by material which suppresses reflection of ultrasonic waves on a boundary surface between the object 011 and the holding member 001. Specifically, material in which a difference between acoustic impedance of the material and that of the object 011 is small is preferably used. For example, a resin material such as polymethylpentene may be used. A thickness of the material is preferably small since the larger the thickness becomes, the larger attenuation becomes when ultrasonic waves passes the holding member 001. However, the material has the thickness enough to hold the object 011.

The ultrasonic waves irradiated to the object 011 are reflected and scattered by the object 011 and return to the piezoelectric elements 024 as echo signals. The echo signals are converted into electric signals and obtained as reception signals by the group of the piezoelectric elements 024 forming the reception opening.

The reception signals are reconstructed as an image by the signal processing unit U 008.

A procedure of processing performed by the signal processing unit U 008 will be described with reference to FIG. 2.

The phasing delay unit 012 determines delay times of the reception signals in accordance with depth information and performs a delay process on the reception signals. The delay times are determined taking not only a structure of the probe 003 and acoustic characteristics of the object 011 but also a thickness and acoustic characteristics of the holding member 001 into consideration.

The reception signals which have been subjected to the delay process are added to one another by an adding unit 013. Thereafter, a combined signal is subjected to Hilbert transform and envelope detection by the Hilbert transform unit 014 and the envelope detection unit 015, respectively, so that an image is reconstructed. Here, the series of processes performed by the signal processing unit U 008 in this embodiment employs a technique of a phasing addition process employed in general ultrasonic diagnostic apparatuses. However, other reconstruction techniques including an adaptive signal process may be efficiently used. Reconstructed image data is subjected to LOG compression performed by the LOG compression unit 016 so that image data for one line is obtained. When the series of processes is performed while a line for generating image data is moved in a lateral direction of the probe 003, a two-dimensional ultrasonic image is reconstructed. The description above illustrates a basic process performed by the signal processing unit U 008 and a filter process and gain control may be performed where appropriate.

A plurality of image data items reconstructed by the signal processing unit U 008 are combined by the image combining unit 009. Note that the plurality of image data items reconstructed by the signal processing unit U 008 may be temporarily stored and combined with one another using a processing apparatus such as a PC when a certain period of time is elapsed after measurement is terminated.

Obtainment of the plurality of image data items will be described hereinafter. Here, although combination rates of the plurality of image data items may be arbitrarily set, a degree of improvement of image quality is changed when the rates are determined in accordance with imaging conditions.

When the series of processes is performed while scanning is performed by the probe 003, three-dimensional image data of an entire region of the object 011 is obtained.

When the combined image is displayed in the image display unit 010, effects of this embodiment may be recognized. Examples of the image display unit 010 include a liquid crystal display, a plasma display, an organic EL display, and an FED. As a display method, not only combined image data but also arbitrary one of the image data items before combining may be displayed or some of the image data items before combining may be displayed in parallel.

Driving of Probe and Imaging Method

A procedure of obtaining an image of the imaging area by successively changing an ultrasonic irradiation area will be described with reference to FIG. 1 and FIGS. 3A to 3C.

The probe 003 is accommodated in the carriage 005 and attached to the driving mechanism 004. The carriage 005 may be moved to an arbitrary position on the holding member 001 by the driving mechanism 004. The driving mechanism 004 includes a motor and a shaft, and a combination of a pulse motor and a ball screw or a linear motor is effectively used.

When the imaging area is determined, the probe 003 passes all over the imaging area as illustrated in FIG. 3A so as to obtain image data. First, the carriage 005 moves from Pos. 1-1 to Pos. 1-2 while image data is obtained. This direction is defined as a main scanning direction. After moving to the Pos. 1-2 at an end of the imaging area, the carriage 005 horizontally moves to Pos. 1-3 and thereafter moves to Pos. 1-4 while obtaining image data. A direction of the horizontal movement is defined as an auxiliary scanning direction. An amount of the horizontal movement is set such that the probe 003 passes the same region in the imaging area at least twice or so as illustrated in FIG. 3B so that image data in the same coordinate is obtained at least twice. For example, the probe 003 passes a noted position illustrated in FIG. 3B twice in a forward path (from Pos. 1-1 to Pos. 1-2) and a backward path (from Pos. 1-3 to Pos. 1-4) while image data is obtained.

Because of a characteristic of a system in which the probe 003 moves back and forth a plurality of times in the main scanning direction in the imaging area, image data items are obtained in the same coordinate in the forward and backward paths of the probe 003 for efficiency. However, the present invention is not limited to this scanning method.

In the image reconstruction, operation of the transmission control unit 007 is changed every time scanning is performed by the probe 003. When individual image data items is reconstructed and thereafter combined with one another, a high-quality image may be obtained. For example, when image data obtained in the forward path (from Pos. 1-1 to Pos. 1-2) and image data obtained in the backward path (from Pos. 1-3 to Pos. 1-4) which correspond to different transmission focus positions are combined with each other, an image having a multistage focus effect is obtained. Furthermore, when image data items obtained by irradiating ultrasonic waves having different center frequencies are combined with each other, an image having a frequency compounding effect may be obtained. Furthermore, when image data items obtained by irradiating ultrasonic waves having patterns of different steering angles are combined with each other, an image having a spatial compounding effect may be obtained.

The effects obtained by combining a plurality of image data items are enhanced when a large number of types of image data are used. Therefore, an amount of movement of the probe 003 in the auxiliary scanning direction is reduced when compared with the scanning method of FIG. 3B or the probe 003 moves back and forth in the main scanning direction a plurality of times before moving in the auxiliary scanning direction. By performing scanning in these ways, types of overlapping image data item in the same coordinate may be increased for efficiency.

Furthermore, when not only the operation of the transmission control unit 007, but also a filter characteristic and a gain value of the signal processing unit U 008 are changed, an effect of image data combining may be enhanced. For example, when ultrasonic waves of different center frequencies are irradiated, bandpass filters corresponding to the center frequencies are employed, and by this, an effect of frequency compounding may be enhanced. Furthermore, when a gain value corresponding to an irradiation condition is set, output values for individual image data items may be uniformed, and an image having negligible unevenness in a depth direction may be obtained by combining.

Change of an imaging condition is effectively performed when a forward movement and a backward movement of the carriage 005 are switched from one to another. Since scanning performed by the probe 003 and imaging are not required to be repeatedly performed while the imaging condition is changed, a processing load of the transmission control unit 007 is reduced, and furthermore, a period of time required for imaging is reduced. Here, if a scale of processing of the transmission control unit 007 and the period of time required for imaging have margins, transmission/reception conditions may be changed a plurality of times in one scanning operation. A case where image data items obtained when ultrasonic waves having positions of transmission focuses of 10 mm, 20 mm, 30 mm, and 40 mm are irradiated are combined with one another will be described with reference to FIGS. 3B and 3C.

As a first imaging procedure, image data items are obtained in an imaging condition of the transmission focus of 10 mm in a forward path (from Pos. 1-1 to Pos. 1-2) and in an imaging condition of the transmission focus of 20 mm in a backward path (from Pos. 1-2 to Pos. 1-1) in FIG. 3C. After the probe 003 horizontally moves to Pos. 1-3, image data items are obtained in an imaging condition of the transmission focus of 30 mm in a forward path (from Pos. 1-3 to Pos. 1-4) and in an imaging condition of the transmission focus of 40 mm in a backward path (from Pos. 1-4 to Pos. 1-3). On the other hand, as a second imaging procedure, image data items are obtained in the imaging conditions of the transmission focuses of 10 mm and 20 mm in a forward path (from Pos. 1-1 to Pos. 1-2) and in the imaging conditions of the transmission focuses of 30 mm and 40 mm in a backward path (from Pos. 1-3 to Pos. 1-4) in FIG. 3B.

In both the imaging procedures, image data items under the four conditions may be obtained. However, although the number of times back and forth movement is performed may be reduced in the latter one, improvement of a scanning speed and reduction of the number of times switching is performed among the imaging conditions may be realized in the former one. Note that when the switching of the imaging conditions is performed, a large table may be required to be read. Therefore, the number of times the switching is performed among the imaging conditions is preferably small.

An embodiment of the present invention addresses problems which arise in an object information acquiring apparatus which performs scanning using a probe along an object when image data items are obtained under different imaging conditions, that is, a problem in which a period of time required for scanning is extended and a problem in which processing is complicated. Specifically, when realization of high image quality is aimed in ultrasonic image apparatuses which perform scanning using a probe, a scanning speed may be lowered and operation may be complicated due to frequent switching of conditions. However, according to an embodiment of the present invention, these problems may be avoided, that is, a high-quality image may be realized while reduction of a scanning speed of a probe and complication caused by switching of conditions are suppressed.

First Embodiment

Hereinafter, the present invention will be described in detail with reference to concrete embodiments.

FIG. 1 is a diagram schematically illustrating a system of an object information acquiring apparatus according to this embodiment.

Configuration of Apparatus

The object information acquiring apparatus includes holding members 001 and 002, an ultrasonic probe 003, a driving mechanism 004, a carriage 005, a driving control unit 006, a transmission control unit 007, a signal processing unit U 008, an image combining unit 009, and an image display unit 010.

Operation of Apparatus

First, a section of an ultrasonic image apparatus will be described. As the ultrasonic probe 003, a linear probe with 128 channels is used. Furthermore, as piezoelectric elements 024, PZTs having a center frequency of 6 MHz are used. A resin flat plate formed by polymethylpentene having a thickness of 7 mm is used as the holding member 001 and an acrylic resin flat plate having a thickness of 10 mm is used as the holding member 002 which holds an object 011 with the holding member 001. The transmission control unit 007 transmits electric signals which form transmission beams in target focus positions to the piezoelectric elements 024. The piezoelectric elements 024 convert the electric signals into ultrasonic signals to be propagated to the object 011. The propagated ultrasonic signals are reflected and scattered by the object 011 and received by the piezoelectric elements 024 which form a reception opening through the holding member 001 as echo signals. In this embodiment, since the reception opening is formed by a group of the 64 piezoelectric elements 024, image data on a scanning line is reconstructed by 64 reception signals. FIG. 5A is a diagram illustrating the positional relationships between a scanning line 021 and the piezoelectric elements 024. The reception signals are supplied to the signal processing unit U 008. The signal processing unit U 008 reconstructs image data on the scanning line 021.

Next, a scanning method will be described.

The probe 003 is accommodated in the carriage 005 and attached to the driving mechanism 004. When an imaging area is set, the driving control unit 006 drives a motor included in the driving mechanism 004 so as to move the carriage 005. In this embodiment, a pulse motor is used as the motor. The carriage 005 may move to an arbitrary position at an arbitrary speed in two axial directions by the driving mechanism 004 including the pulse motor and a ball screw. As a passage route of the carriage 005, as illustrated in FIG. 3B, the probe 003 moves back and forth so as to obtain an ultrasonic image in the same coordinate (same position) at least twice.

In this embodiment, the carriage 005 moves by 10 mm in the auxiliary scanning direction (from Pos. 1-2 to Pos. 1-3). Here, a width of linear scanning performed when image data is obtained is set to approximately 25 mm so that image data in the same coordinate in the imaging area is obtained at least twice.

Actual movement of the carriage 005 and a timing when an image is obtained will be described. First, in the forward path from Pos. 1-1 to Pos. 1-2, the transmission control unit 007 is driven so that a transmission focus depth of 5 mm is attained. After arriving at Pos. 1-2, the probe 003 moves to Pos. 1-3 by 10 mm. In the backward path from Pos. 1-3 to Pos. 1-4, the transmission control unit 007 is driven so that a transmission focus depth of 15 mm is attained. After arriving at Pos. 1-4, the probe 003 moves to Pos. 1-5 by 10 mm, and thereafter, a process of alternately obtaining image data items corresponding to the transmission focus depth of 5 mm and the transmission focus depth of 15 mm is repeatedly performed while the probe 003 moves all over the imaging area. Since the image data items are combined by the image combining unit 009 in accordance with the depths, an image having a multistage focus effect may be realized. Here, since the number of times switching of transmission conditions is performed is reduced and image data items are collectively output for individual scanning operations performed by the probe 003, entire processing is facilitated.

Furthermore, when an image in a deeper region is obtained, an image of high resolution even in a deep portion may be realized by increasing the number of conditions of a transmission focus position. When an image region to a depth of 40 mm is to be obtained, as a passage route of the carriage 005 in this embodiment, the probe 003 moves back and forth so that an ultrasonic image in the same coordinate is obtained at least four times as illustrated in FIG. 3C.

In this embodiment, the carriage 005 moves by 10 mm in the auxiliary scanning direction (from Pos. 1-1 to Pos. 1-3). Here, a width of linear scanning performed when image data is obtained is set to approximately 25 mm so that image data in the same coordinate in the imaging area is obtained at least four times.

Actual movement of the carriage 005 and a timing when an image is obtained will be described. First, in a forward path from Pos. 1-1 to Pos. 1-2, the transmission control unit 007 is driven so that a transmission focus depth of 5 mm is attained. After arriving at Pos. 1-2, the carriage 005 does not move in the auxiliary direction but moves to Pos. 1-1. In this backward path, the transmission control unit 007 is driven so that a transmission focus of 15 mm is set. After arriving at Pos. 1-1, the probe 003 moves to Pos. 1-3 by 10 mm. In a forward path from Pos. 1-3 to Pos. 1-4, the transmission control unit 007 is driven so that a transmission focus depth of 25 mm is attained. After arriving at Pos. 1-4, the carriage 005 does not move in the auxiliary direction but moves to Pos. 1-3. In this backward path, the transmission control unit 007 is driven so that a transmission focus of 35 mm is set.

After arriving at Pos. 1-3, the carriage 005 moves to Pos. 1-5 by 10 mm, and thereafter, a process of alternately obtaining image data items corresponding to the transmission focus depths of 5 mm, 15 mm, 25 mm, and 35 mm is repeatedly performed so that the carriage 005 moves all over the imaging area.

By the series of processes, four focus types of image data are obtained from the entire imaging region, and when the four focus types of image data are combined with one another, a multistage focus image having four stages in a depth of 40 mm at most may be realized.

Furthermore, an image having transmission focuses of two stages may be obtained by a single scanning operation. In the scanning pattern illustrated in FIG. 3B in this embodiment, when scanning is performed from Pos. 1-1 to Pos. 1-2, two types of images, that is, an image of a transmission focus of 5 mm and an image of a transmission focus of 15 mm, are obtained whereas when scanning is performed from Pos. 1-3 to Pos. 1-4, two types of images, that is, an image of a transmission focus of 25 mm and an image of a transmission focus of 35 mm, are obtained. An image of a four-stage focus may be realized by performing image capturing in this way. Note that, when a plurality of images are obtained by a single scanning operation, the number of times switching of conditions is performed is increased, and therefore, processing and data output are complicated. Accordingly, the number of types of image capturing is preferably reduced when such scanning is performed.

Furthermore, in this embodiment, a reception condition is changed depending on data. In this embodiment, a bandpass filter having a center frequency of 7 MHz is used for the image corresponding to the transmission focus of 15 mm and a bandpass filter having a center frequency of 5 MHz is used for the image corresponding to the transmission focus of 40 mm. Furthermore, different gain values are also employed. This is because unevenness of output values is avoided when a plurality of image data items are combined with one another.

The system described above is used in practice. As a result, an ultrasonic image which realizes a multistage focus may be obtained while lowering of a scanning speed of a probe or complicated operation caused by switching of conditions are suppressed.

Second Embodiment

A configuration of an apparatus and basic operation of the apparatus are the same as those of the first embodiment, but this embodiment is different from the first embodiment only in that center frequencies of transmission waves at times of back and forth scanning are different from one another. A carriage 005 in this embodiment moves back and forth so that a probe 003 obtains an ultrasonic image in the same coordinate at least four times as illustrated in FIG. 3C. When scanning is performed from Pos. 1-1 to Pos. 1-2, a transmission waveform having a center frequency of 5 MHz is irradiated whereas when scanning is performed from Pos. 1-2 to Pos. 1-1, a transmission waveform having a center frequency of 6 MHz is irradiated. After the carriage 005 moves to Pos. 1-3, when scanning is performed from Pos. 1-3 to Pos. 1-4, a transmission waveform having a center frequency of 7 MHz is irradiated whereas when scanning is performed from Pos. 1-4 to Pos. 1-3, a transmission waveform having a center frequency of 8 MHz is irradiated. Four types of image data which have different transmission frequencies and which are generated by the process described above are combined with one another by an image combining unit 009. A combining rate may be arbitrarily set. However, in this embodiment, the images are uniformly combined in a ratio of 25% in a shallow portion and rates of the images having the center frequencies of 5 MHz and 6 MHz are increased in a portion deeper than 30 mm. When not only the irradiation condition but also content of the processing performed by the signal processing unit U 008 is changed, an effect may be enhanced. In this embodiment, the bandpass filters having center frequencies of 5 MHz, 6 MHz, 7 MHz, and 8 MHz corresponding to the transmission frequencies are employed in a filter processing unit 017 illustrated in FIG. 4.

The system described above is used in practice. As a result, an ultrasonic image which attains a frequency compounding effect may be obtained while lowering of a scanning speed of a probe or complicated operation caused by switching of conditions are suppressed.

Third Embodiment

Figure 5B:
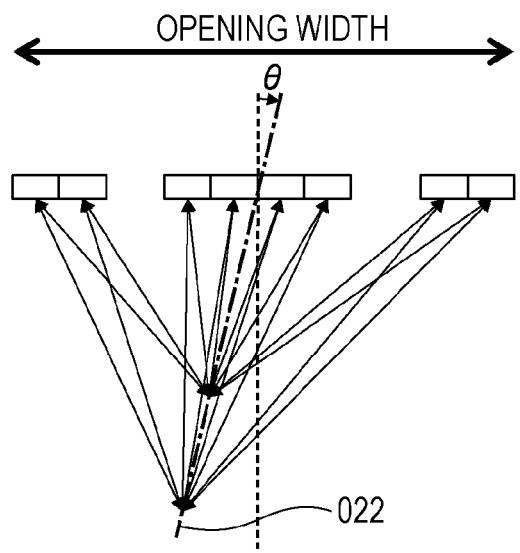

A configuration of an apparatus and basic operation of the apparatus are the same as those of the first embodiment, but this embodiment is different from the first embodiment only in that steering directions (steering angles θ (illustrated in FIG. 5B)) of ultrasonic irradiation at times of back and forth scanning are different from one another. A carriage 005 in this embodiment moves back and forth so that a probe 003 obtains an ultrasonic image in the same coordinate at least four times as illustrated in FIG. 3C. When scanning is performed from Pos. 1-1 to Pos. 1-2, irradiation is performed in a transmission pattern in which a steering angle θ is −10 degrees whereas when scanning is performed from Pos. 1-2 to Pos. 1-1, irradiation is performed in a transmission pattern in which a steering angle θ is 10 degrees. After the carriage 005 moves from Pos. 1-1 to Pos. 1-3, when scanning is performed from Pos. 1-3 to Pos. 1-4, irradiation is performed in a transmission pattern in which a steering angle θ is 0 degree whereas when scanning is performed from Pos. 1-4 to Pos. 1-3, an ultrasonic wave is not irradiated. The transmission patterns which realize the steering angles θ are controlled by a transmission control unit 007. Reception signals obtained in the individual steps are reconstructed by a signal processing unit U 008 and combined with one another in an arbitrary rate by an image combining unit 009. In this embodiment, the reception signals are uniformly combined with one another in a ratio of 33%.

When not only the irradiation condition but also content of the processing performed by the signal processing unit U 008 is changed, an effect may be enhanced. In this embodiment, a phasing delay unit 012 performs a delay process of focusing on a scanning line 022 of FIG. 5B. Since the delay process generates distortion of image data items, an image combining unit 009 performs affine deformation processes corresponding to the steering angles θ so as to correct distortion of image data items before the image data items are combined with one another.

Here, since captured regions are different from one another depending on the steering angles θ, when the combining is simply performed, some portions may not overlap with each other. In this embodiment, a large scanning region is subjected to image capturing so that a display region is subjected to image capturing under any condition.

Furthermore, the beam steering angles θ are effectively inclined not only in an auxiliary scanning direction but also in a main scanning direction. FIG. 10 is a diagram illustrating a state in which a transmission beam is inclined in the main scanning direction.

The carriage 005 in this embodiment moves back and forth so that the probe 003 obtains an ultrasonic image in the same coordinate at least four times as illustrated in FIG. 3C. When scanning is performed from Pos. 1-1 to Pos. 1-2, irradiation is performed in a transmission pattern in which a steering angle θ is −10 degrees whereas when scanning is performed from Pos. 1-2 to Pos. 1-1, irradiation is performed in a transmission pattern in which a steering angle θ is 10 degrees. After the carriage 005 moves from Pos. 1-1 to Pos. 1-3, when scanning is performed from Pos. 1-3 to Pos. 1-4, irradiation is performed in a transmission pattern in which a steering angle θ is 0 degree whereas when scanning is performed from Pos. 1-4 to Pos. 1-3, an ultrasonic wave is not irradiated.

Steering of a transmission beam is realized by disposing a driving system capable of controlling inclination of the probe 003 in the main scanning direction in the carriage 005 and controlling the driving system by the driving control unit 006. Although a servo motor is used in this embodiment, any actuator may be used as long as inclination of the probe 003 is controlled. Furthermore, a 1.5D-probe may be used as the probe 003, and a beam is steered in the main scanning direction by controlling the transmission control unit 007.

Even when a beam is inclined in the main scanning direction, a process to be performed on obtained image data items is the same as the process employed when a beam is inclined in a lateral direction.

The system described above is used in practice. As a result, an ultrasonic image which attains a spatial compounding effect may be obtained while lowering of a scanning speed of a probe or complicated operation caused by switching of conditions are suppressed.

Fourth Embodiment

A configuration of an apparatus and basic operation of the apparatus are the same as those of the first embodiment, but this embodiment is different from the first embodiment only in that transmission apodization is changed at times of back and forth scanning. As a passage route of a carriage 005 of this embodiment, as illustrated in FIG. 3B, a probe 003 moves back and forth so as to obtain an ultrasonic image in the same coordinate at least twice. First, in a forward path from Pos. 1-1 to Pos. 1-2, a transmission control unit 007 is driven while elements in a transmission opening are uniformly weighted. After arriving at Pos. 1-2, the probe 003 moves to Pos. 1-3 by 10 mm. In a backward path from Pos. 1-3 to Pos. 1-4, the transmission control unit 007 is driven while Hamming weights are assigned to the elements in the transmission opening. Two types of image data which have different types of apodization and which are generated by the process described above are combined with one another by an image combining unit 009. As a combining method in this embodiment, a method for comparing output values in the same position of two images with each other and employing a smaller output value is employed. By this combining, an image having higher resolution and suppressing side lobes is realized. Combination of types of apodization may be arbitrary set. Furthermore, the effect of apodization may be enhanced not only by changing an irradiation condition but also by weighting the individual elements by an adding unit 013 included in a signal processing unit U 008. In this embodiment, weights are not assigned to the individual elements in the forward path from Pos. 1-1 to Pos. 1-2 whereas Hamming weights are assigned to the individual elements in the backward path from Pos. 1-3 to Pos. 1-4.

When the system described above is used in practice, an ultrasonic image which has high resolution and which suppresses side lobes may be realized while lowering of a scanning speed of a probe or complicated operation caused by switching of conditions are suppressed.

Fifth Embodiment

Figure 5C:
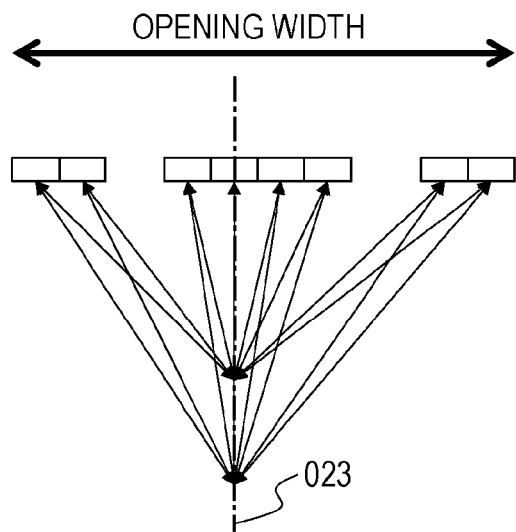

A configuration of an apparatus and basic operation of the apparatus are the same as those of the first embodiment, but this embodiment is different from the first embodiment only in that a position of an image capturing line is changed at times of back and forth scanning. As a passage route of a carriage 005 of this embodiment, as illustrated in FIG. 3B, a probe 003 moves back and forth so as to obtain an ultrasonic image in the same coordinate at least twice. In a forward path from Pos. 1-1 to Pos. 1-2, a scanning line 021 corresponds to the center of a transmission opening as illustrated in FIG. 5A whereas in a backward path from Pos. 1-3 to Pos. 1-4, a scanning line 023 corresponds to a portion shifted from the center of the transmission opening by half of an element as illustrated in FIG. 5C. The change of a scanning line is performed by controlling delay times determined by a transmission control unit 007 and a phasing delay unit 012. Individual reconstructed image data items are combined with each other in the image combining unit 009. Since the scanning lines 021 and 023 are shifted from each other in a lateral direction by a half pitch, an image having a small line pitch is realized by alternately rearranging the image data items. An amount of shift of the scanning line is not limited to a half pitch. Furthermore, when a passage route of the carriage 005 is changed, the number of times an ultrasonic image in the same coordinate is obtained is increased, and an amount of shift of the scanning line is changed, an image having a smaller line pitch may be obtained.

The system described above is used in practice. As a result, an ultrasonic image having a small lateral pitch may be obtained while lowering of a scanning speed of a probe or complicated operation caused by switching of conditions are suppressed.

Sixth Embodiment

Figure 6:
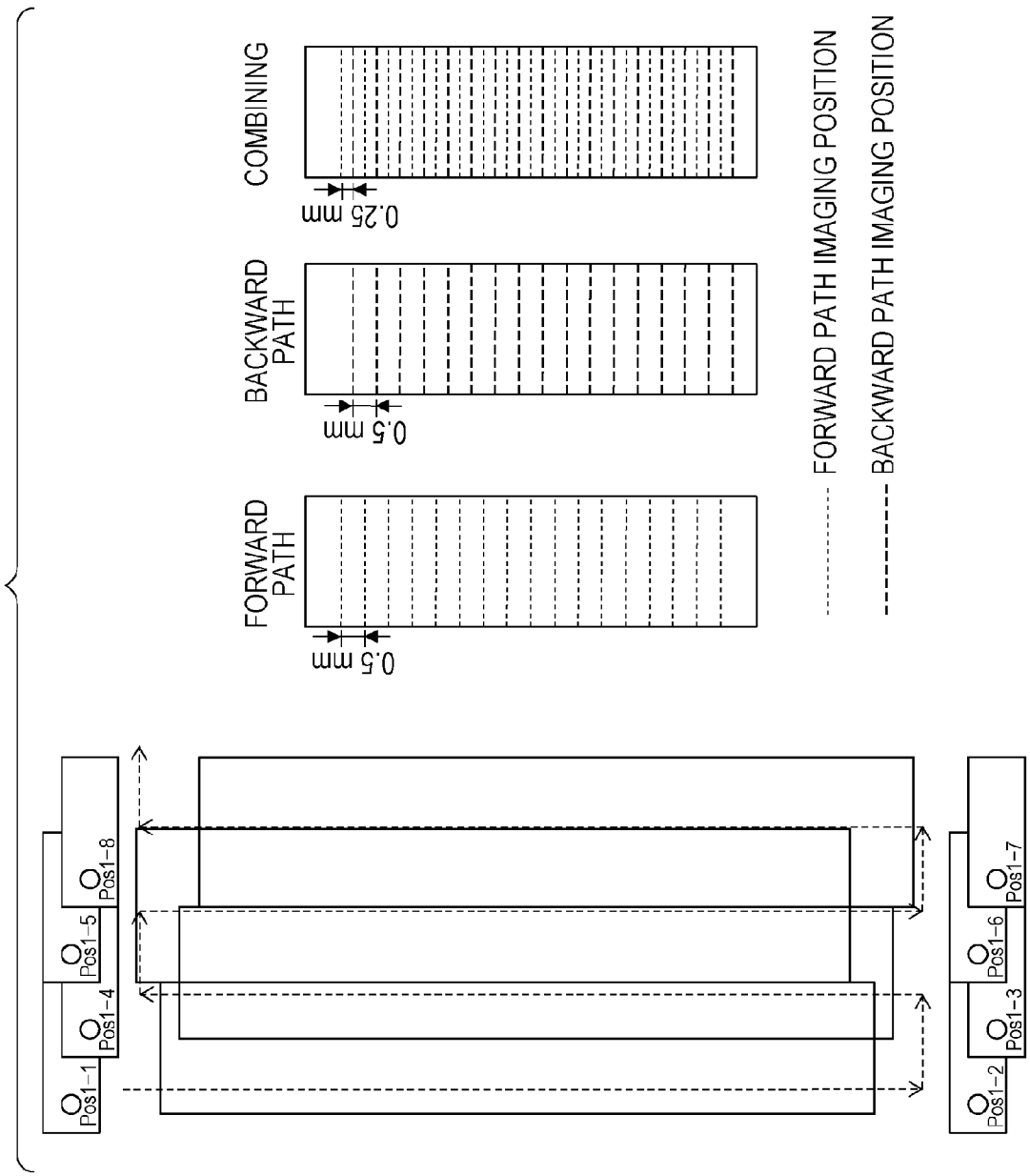
FIG. 6 is a diagram illustrating reception timings of reflected ultrasonic waves according to an embodiment of the present invention.

A configuration of an apparatus and basic operation of the apparatus are the same as those of the first embodiment, but this embodiment is different from the first embodiment only in that a timing of image capturing is changed at times of back and forth scanning. As a passage route of a carriage 005 of this embodiment, as illustrated in FIG. 3B, a probe 003 moves back and forth so as to obtain an ultrasonic image in the same coordinate at least twice. In a forward path from Pos. 1-1 to Pos. 1-2, image capturing is performed every 0.50 mm in a carriage scanning direction whereas in a backward path from Pos. 1-3 to Pos. 1-4, image capturing is performed in positions shifted by 0.25 mm relative to positions where the image capturing is performed in the forward path as illustrated in FIG. 6. Individual reconstructed image data items are combined with each other in an image combining unit 009. By alternately selecting the reconstructed image data items by lines in a main scanning direction, an image having a small pitch in the main scanning direction may be realized. An amount of change of the image capturing timing is not limited to the numeric value described above. Furthermore, when a passage route of the carriage 005 is changed, the number of times an ultrasonic image in the same coordinate is obtained is increased, and change of the image capturing timing is performed a plurality of times, an image having a smaller pitch may be obtained.

The system described above is used in practice. As a result, an ultrasonic image having a small pitch in the main scanning direction may be obtained while lowering of a scanning speed of a probe or complicated operation caused by switching of conditions are suppressed.

Seventh Embodiment

Figure 7:
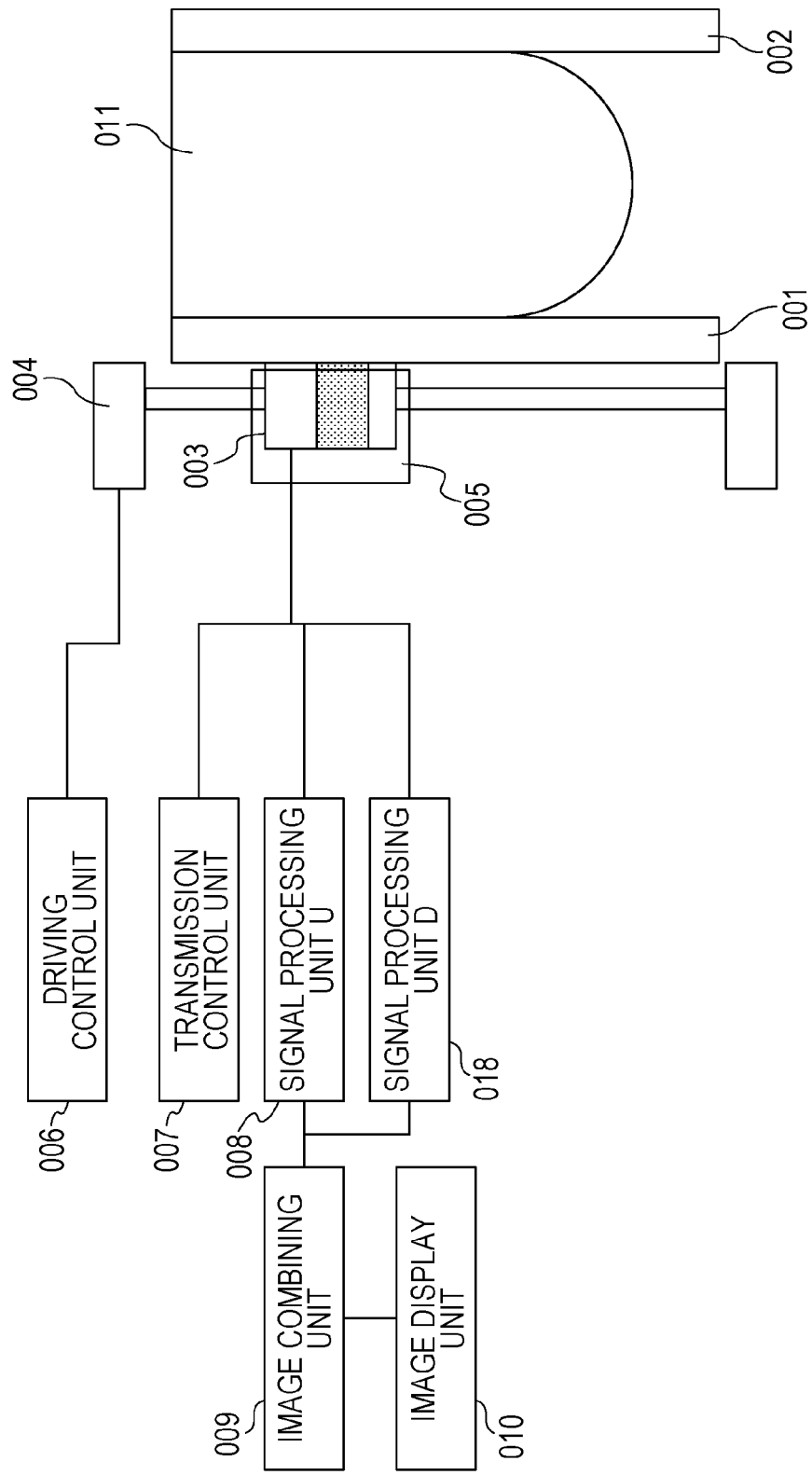
FIG. 7 is a diagram illustrating another configuration of the object information acquiring apparatus according to an embodiment of the present invention.

A configuration of an apparatus and basic operation of the apparatus are the same as those of the first embodiment, but this embodiment is different from the first embodiment in that the apparatus includes a signal processing unit D 018 as illustrated in FIG. 7 which has a Doppler function and which obtains a Doppler image. As a passage route of a carriage 005 of this embodiment, as illustrated in FIG. 3B, a probe 003 moves back and forth so as to obtain an ultrasonic image in the same coordinate at least twice. In a forward path from Pos. 1-1 to Pos. 1-2, image data described in the first to sixth embodiments is captured. In a backward path from Pos. 1-3 to Pos. 1-4, the signal processing unit D 018 generates an image of blood flow using an ultrasonic Doppler method. Although color Doppler is employed as the ultrasonic Doppler method in this embodiment, other Doppler methods including power Doppler may be used. The image data obtained in the forward path and the image of blood flow obtained in the backward path are combined with each other by an image combining unit 009 and a resultant superimposed image is displayed by an image display unit 010.

Accuracy of the image of blood flow is changed depending on angles of an irradiation direction of an ultrasonic wave and directions of blood vessels. Therefore, blood flow data of low accuracy may be obtained depending on an irradiation angle. To improve the accuracy of blood flow data, blood flow data items are obtained by changing an irradiation direction of an ultrasonic wave irradiated from the ultrasonic probe 003 at least twice and the obtained blood flow data items are combined with each other in this embodiment.

The carriage 005 in this embodiment moves back and forth so that an ultrasonic image in the same coordinate is obtained at least four times as illustrated in FIG. 3C. In a forward path from Pos. 1-1 to Pos. 1-2 and a backward path from Pos. 1-2 to Pos. 1-1, image data items described in the first to sixth embodiments are captured. In a forward path from Pos. 1-3 to Pos. 1-4 and a backward path from Pos. 1-4 to Pos. 1-3, blood flow data is obtained. In the forward path in which the blood flow data is obtained, an irradiation angle of an ultrasonic wave is inclined by 10 degrees relative to a main scanning direction as illustrated in FIG. 10. As a method for inclining the ultrasonic wave irradiation angle, as with the beam steering method described in the third embodiment, a driving system capable of controlling inclination of the probe 003 in the main scanning direction is disposed in the carriage 005 and the driving system is controlled by the driving control unit 006. As described in the third embodiment, a 1.5D-probe may be used as the probe 003, and a beam is steered in the main scanning direction by controlling the transmission control unit 007 for efficiency.

The signal processing unit D 018 performs correction on image information of the forward path and image information of the backward path by inclination angles so that positions in the forward and backward paths correspond to each other. Obtained image data and blood flow data are combined with each other by the image combining unit 009 and a resultant superimposed image is displayed in the image display unit 010.

Although the inclination angle is 10 degrees in this embodiment, this angle may be arbitrarily set. Furthermore, in addition to superimposing of the image data and the blood flow data, an arbitrary image position may be specified and a blood flow value in the position may be efficiently displayed.

The system described above is used in practice. As a result, an ultrasonic image and Doppler information may be obtained and superimposed display may be performed while lowering of a scanning speed of a probe or complicated operation caused by switching of conditions are suppressed.

Eighth Embodiment

Figure 8:
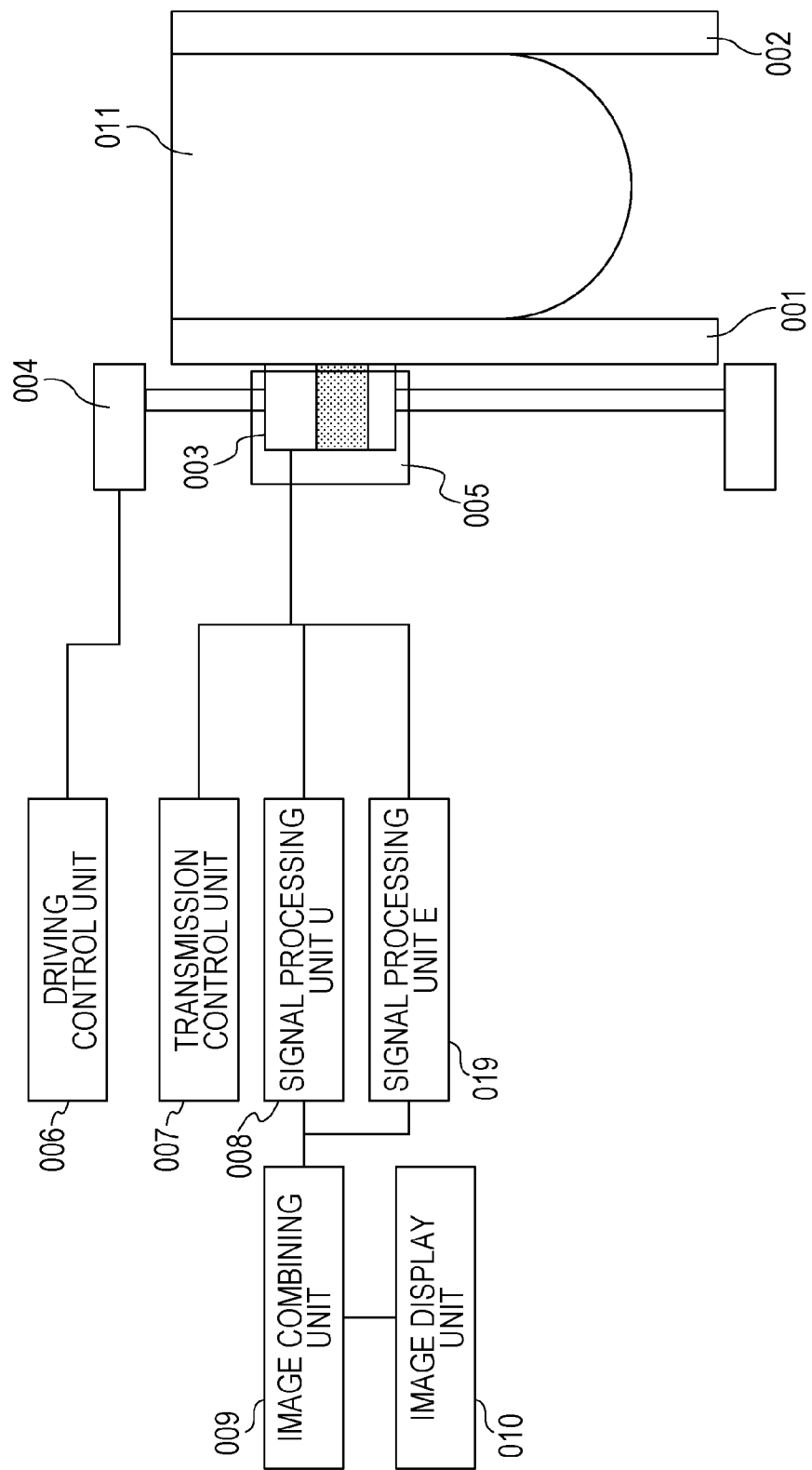
FIG. 8 is a diagram illustrating a further configuration of the object information acquiring apparatus according to an embodiment of the present invention.

A configuration of an apparatus and basic operation of the apparatus are the same as those of the first embodiment, but this embodiment is different from the first embodiment in that an apparatus includes a signal processing unit E 019 as illustrated in FIG. 8 which has an elastography function and which obtains an elastographic image. As a passage route of a carriage 005 of this embodiment, as illustrated in FIG. 3B, a probe 003 moves back and forth so as to obtain an ultrasonic image in the same coordinate at least twice. In a forward path from Pos. 1-1 to Pos. 1-2, image data described in the first to sixth embodiments is obtained. In a backward path from Pos. 1-3 to Pos. 1-4, a transmission control unit 007 is driven so that a continuous wave is irradiated from the probe 003. A propagation speed of an elastic wave generated at the irradiation is detected and information on the propagation speed is processed by the signal processing unit E 019 so that hardness data of an object at an irradiation spot is obtained. In this embodiment, a continuous wave of 4 MHz is irradiated, and the signal processing unit E 019 generates hardness data by converting a numeric value of hardness and information on the hardness into color for each irradiation spot. The obtained image data and the hardness data are combined with each other by an image combining unit 009 and a superimposed image is displayed in an image display unit 010. Here, changing of a superimposing may be performed by a setting and the hardness data is represented by a numeric value or color information where appropriate. In this embodiment, a method for calculating hardness data by measuring a propagation speed of an elastic wave is employed. However, a method for measuring information on hardness by measuring distortion generated by irradiated sound pressure of an ultrasonic wave may be effectively used.

The system described above is used in practice. As a result, an ultrasonic image and hardness information may be obtained and superimposed display may be performed while lowering of a scanning speed of a probe or complicated operation caused by switching of conditions are suppressed.

Ninth Embodiment

Figure 9:
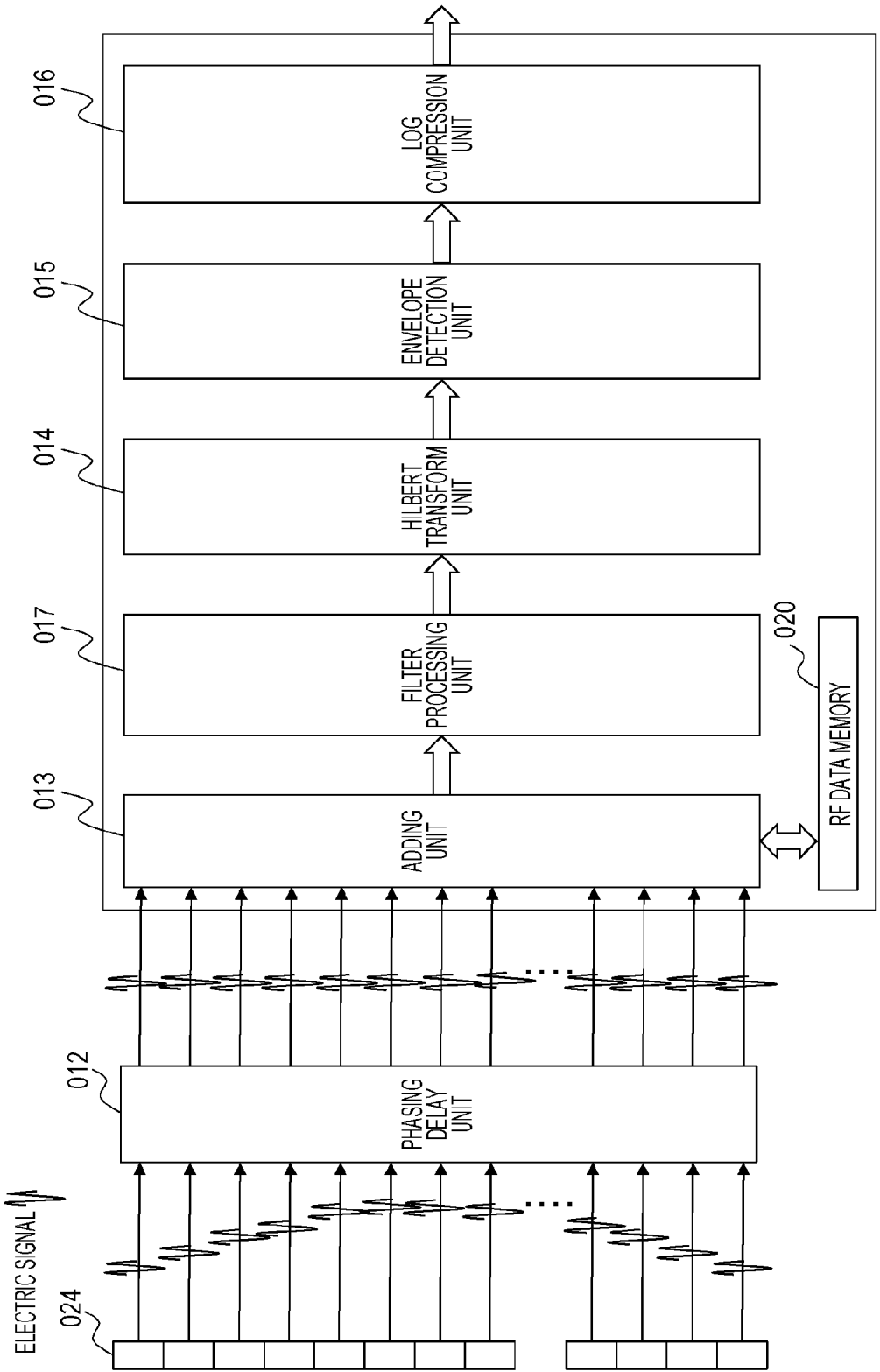
FIG. 9 is a diagram illustrating a further configuration of the signal processing unit according to an embodiment of the present invention.

A configuration of an apparatus and basic operation of the apparatus are the same as those of the first embodiment, but this embodiment is different from the first embodiment in that the apparatus includes an RF data memory 020 as illustrated in FIG. 9, and therefore, the apparatus includes a system capable of temporarily storing RF signals independently obtained in forward and backward scanning and performing a combining process. As a passage route of a carriage 005 of this embodiment, as illustrated in FIG. 3B, a probe 003 moves back and forth so as to obtain an ultrasonic image in the same coordinate at least twice. In a forward path from Pos. 1-1 to Pos. 1-2, an ultrasonic wave which is positively and negatively oscillated is irradiated. Echo signals obtained by the probe 003 are added to one another by an adding unit 013 before being stored in the RF data memory 020. In a backward path from Pos. 1-3 to Pos. 1-4, ultrasonic waves having phases shifted by 180 degrees relative to phases of waveforms in the forward path are irradiated. Echo signals obtained by the probe 003 are added to one another by the adding unit 013 before being added to an RF signal which has been obtained in the forward path and which has been stored in the RF data memory 020. A resultant RF signal obtained by the addition is processed by a bandpass filter supporting higher harmonic waves included in a filter processing unit 017 before reconstructed image data is obtained. Since normal image data may be generated without adding RF data, the image data and higher harmonic wave image data may be combined with each other by the image combining unit 009 and a superimposed image may be displayed in the image display unit 010, or images may be individually output without combining. In this embodiment, the RF data memory 020 is used to realize a harmonic image by a phase inversion method. In this case, the probe 003 having a sensitivity characteristic in which basic waves and higher harmonic waves may be received is used.

The system described above is used in practice. As a result, a higher harmonic wave image and a B-mode image may be obtained and superimposed display may be performed while lowering of a scanning speed of a probe or complicated operation caused by switching of conditions are suppressed.

According to an embodiment of the present invention, a high-quality image may be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-062580, filed Mar. 25, 2013 which is hereby incorporated by reference herein in its entirety.

What is claimed is:

1. An object information acquiring apparatus, comprising:
   a probe configured to irradiate an ultrasonic irradiation region of an object with ultrasonic waves, receive ultrasonic echoes from the object, and convert the ultrasonic echoes into electric signals;
   a driving control unit configured to control a driving mechanism configured to move the probe along a plurality of paths to perform scanning of the object;
   an ultrasonic control unit configured to control irradiation of ultrasonic waves to the object performed by the probe;
   a signal processing unit configured to generate a line for an ultrasonic image based on the electric signals from the probe as the probe moves along each path among the plurality of paths; and
   a combining unit configured to combine a plurality of ultrasonic images obtained by the signal processing unit,
   wherein the driving control unit causes the probe to move along:
      a first path by moving the probe in a first direction; and
      a second path by moving the probe in a second direction different from the first direction,
      wherein the driving control unit alternates between causing the probe to move along a first set of paths parallel to the first path in the first direction and causing the probe to move along a second set of paths parallel to the second path in the second direction;
   wherein at least a portion of the ultrasonic irradiation region of the probe in the first path and at least a portion of the ultrasonic irradiation region of the probe in the second path overlap each other,
   the ultrasonic control unit employs different ultrasonic-wave irradiation conditions for the probe as the probe is moved in the first direction than the ultrasonic-wave irradiation conditions for the probe as the probe is moved in the second direction,
   the combining unit combines a plurality of ultrasonic images obtained in accordance with electric signals based on ultrasonic waves irradiated with the different ultrasonic-wave irradiation conditions,
   wherein the ultrasonic-wave irradiation conditions include at least one of a focus position of the ultrasonic waves, a focus depth of the ultrasonic waves, a center frequency of the ultrasonic waves, a steering direction of the ultrasonic waves, and a transmission apodization of the ultrasonic waves.

2. The object information acquiring apparatus according to claim 1, wherein
   the signal processing unit uses different processing parameters to generate the lines for the ultrasonic image based on the electric signals from the probe as the probe moves in the first direction than the processing parameters used to generate the lines for the ultrasonic image based on the electric signals from the probe as the probe moves in the second direction.

3. The object information acquiring apparatus according to claim 2, wherein
   the processing parameters include filter characteristics of a filtering process to which the electric signals are subjected, or gains applied to the electric signals.

4. The object information acquiring apparatus according to claim 1, wherein
   the ultrasonic control unit employs different ultrasonic-wave irradiation conditions so that focus positions of the ultrasonic waves as the probe moves in the first direction are different from focus positions of the ultrasonic waves as the probe moves in the second direction.

5. The object information acquiring apparatus according to claim 4, wherein
   the focus positions of the ultrasonic waves correspond to focus depths.

6. The object information acquiring apparatus according to claim 1, wherein
   the ultrasonic wave control unit employs different ultrasonic-wave irradiation conditions so that frequencies of the ultrasonic waves as the probe moves in the first direction are different from frequencies of the ultrasonic waves as the probe moves in the second direction.

7. The object information acquiring apparatus according to claim 6, wherein the combining unit sets a combination ratio of the plurality of ultrasonic images according to a depth within the object.

8. The object information acquiring apparatus according to claim 1, wherein
   the ultrasonic control unit employs different ultrasonic-wave irradiation conditions so that irradiation directions (steering directions) of the ultrasonic waves as the probe moves in the first direction are different from irradiation directions (steering directions) of the ultrasonic waves as the probe moves in the second direction.

9. The object information acquiring apparatus according to claim 8, wherein the irradiation direction of the ultrasonic wave is controlled by controlling inclination of the probe to be different as the probe is moved in a first direction than the inclination of the probe as the probe is moved in the second direction.

10. The object information acquiring apparatus according to claim 8, wherein the irradiation direction of the ultrasonic wave is controlled by controlling the transmission parameters for a 1.5D probe.

11. The object information acquiring apparatus according to claim 8, wherein the combining unit performs correction on the combined image.

12. The object information acquiring apparatus according to claim 1, wherein
   an ultrasonic image obtained by the signal processing unit is a Doppler image.

13. The object information acquiring apparatus according to claim 1, wherein
   an ultrasonic image obtained by the signal processing unit is an elastographic image.

14. The ultrasound apparatus according to claim 1, wherein the first direction and the second direction are opposite to each other.

15. The object information acquiring apparatus according to claim 14, wherein the driving control unit is further configured to control the driving mechanism to move the probe in a third direction that intersects the first direction and the second direction.

16. The ultrasound apparatus according to claim 1, wherein the ultrasonic control unit is further configured to switch the ultrasonic-wave irradiation conditions after the probe is move in the first direction and prior to the probe moving in the second direction.

17. The object information acquiring apparatus according to claim 1, wherein the ultrasonic control unit employs the ultrasonic-wave irradiation conditions such that transmission apodization is different as the probe is moved in the first direction than the transmission apodization as the probe is moved in the second direction.

18. The object information acquiring apparatus according to claim 17, wherein the combining unit employs a smaller one of the values of a value obtained when the probe is moved in the first direction and a value obtained when the probe is moved in the second direction.

19. The object information acquiring apparatus according to claim 1, wherein
the signal processing unit is further configured to:
obtain a first type of image data when the probe is moved in the first direction; and
obtain a second type of image data when the probe is moved in the second direction; and
wherein the second type of image data is different from the first type of image data; and
the combining unit is further configured to combine the first type of image data and the second type of image data.

20. The object information acquiring apparatus according to claim 1, wherein
the signal processing unit is further configured to:
obtain a first type of image data when the probe is moved in the first direction along the first path;
obtain a second type of image data when the probe is moved in the second direction along the second path;
obtain a third type of image data when the probe is moved in the first direction along a third path;
obtain a fourth type of image data when the probe is moved in the second direction along a fourth path; and
wherein the first type of image data, the second type of image data; the third type of image data, and the fourth type of image data are all different from each other; and
the combining unit is further configured to combine the first type of image data, the second type of image data; the third type of image data, and the fourth type of image data.

21. A controller of an ultrasound apparatus having a probe and a driving control unit configured to control a driving mechanism configured to move the probe to perform scanning on an object, wherein the probe is configured to irradiate an ultrasonic irradiation region of an object with ultrasonic waves, receive ultrasonic echoes from the object, and convert the ultrasonic echoes into electric signals, the controller comprises:
an ultrasonic control unit configured to control irradiation of ultrasonic waves to the object performed by the probe;
a signal processing unit configured to generate a line for an ultrasonic image based on the electric signals from the probe as the probe moves along each path among the plurality of paths; and
a combining unit configured to combine a plurality of ultrasonic images obtained by the signal processing unit,
wherein the driving control unit causes the probe to move along:
a first path by moving the probe in a first direction; and
a second path by moving the probe in a second direction different from the first direction,
wherein the driving control unit alternates between causing the probe to move along a first set of paths parallel to the first path in the first direction and causing the probe to move along a second set of paths parallel to the second path in the second direction;
wherein at least a portion of the ultrasonic irradiation region of the probe in the first path and at least a portion of the ultrasonic irradiation region of the probe in the second path overlap each other,
the ultrasonic control unit employs different ultrasonic-wave irradiation conditions for the probe as the probe is moved in the first direction than the ultrasonic-wave irradiation conditions for the probe as the probe is moved in the second direction, and
the combining unit combines a plurality of ultrasonic images obtained in accordance with electric signals based on ultrasonic waves irradiated with the ultrasonic-wave irradiation conditions,
wherein the ultrasonic-wave irradiation conditions include at least one of a focus position of the ultrasonic waves, a focus depth of the ultrasonic waves, a center frequency of the ultrasonic waves, a steering direction of the ultrasonic waves, and a transmission apodization of the ultrasonic waves.

22. The controller according to claim 21, wherein
the signal processing unit uses different processing parameters to generate the lines for the ultrasonic image based on the electric signals from the probe as the probe moves in the first direction than the processing parameters used to generate the lines for the ultrasonic image based on the electric signals from the probe as the probe moves in the second direction.

23. The controller according to claim 22, wherein
the processing parameters include filter characteristics of a filtering process to which the electric signals are subjected, or gains applied to the electric signals.

24. The controller according to claim 21, wherein
the ultrasonic control unit employs different ultrasonic-wave irradiation conditions so that focus positions of the ultrasonic waves as the probe moves in the first direction are different from focus positions of the ultrasonic waves as the probe moves in the second direction.

25. The controller according to claim 24, wherein
the focus positions of the ultrasonic waves correspond to focus depths.

26. The controller according to claim 21, wherein
the ultrasonic wave control employs different ultrasonic-wave irradiation conditions unit so that frequencies of the ultrasonic waves as the probe moves in the first direction are different from frequencies of the ultrasonic waves as the probe moves in the second direction.

27. The object information acquiring apparatus according to claim 26, wherein the combining unit sets a combination ratio of the plurality of ultrasonic images according to a depth within the object.

28. The controller according to claim 21, wherein
the ultrasonic control unit employs different ultrasonic-wave irradiation conditions so that irradiation directions (steering directions) of the ultrasonic waves as the probe moves in the first direction are different from irradiation directions (steering directions) of the ultrasonic waves as the probe moves in the second direction.

29. The controller according to claim 28, wherein the combining unit performs correction on the combined image.

30. The controller according to claim 21, wherein the first direction and the second direction are opposite to each other.

31. The controller according to claim 30, further configured to control the driving mechanism to move the probe in a third direction that intersects the first direction and the second direction.

32. The controller according to claim 21, wherein the ultrasonic control unit is further configured to switch the ultrasonic-wave irradiation conditions after the probe is move in the first direction and prior to the probe moving in the second direction.

33. The controller according to claim 21, wherein the ultrasonic control unit employs the ultrasonic-wave irradiation conditions such that transmission apodization is different as the probe is moved in the first direction than the transmission apodization as the probe is moved in the second direction.

34. The controller according to claim 33, wherein the combining unit employs a smaller one of the values of a value obtained when the probe is moved in the first direction and a value obtained when the probe is moved in the second direction.

\* \* \* \* \*